(12) United States Patent
Mohajerzadeh et al.

(10) Patent No.: US 8,642,371 B2
(45) Date of Patent: Feb. 4, 2014

(54) METHOD AND SYSTEM FOR FABRICATING ION-SELECTIVE FIELD-EFFECT TRANSISTOR (ISFET)

(76) Inventors: Shamsoddin Mohajerzadeh, Tehran (IR); Mehran Shahmohammdi, Tehran (IR); Nina Zehfroosh, Tehran (IR)

( * ) Notice: Subject to any disclaimer, the term of this patent is extended or adjusted under 35 U.S.C. 154(b) by 131 days.

(21) Appl. No.: 13/244,488

(22) Filed: Sep. 25, 2011

(65) Prior Publication Data

US 2012/0258560 A1    Oct. 11, 2012

Related U.S. Application Data

(60) Provisional application No. 61/472,283, filed on Apr. 6, 2011.

(51) Int. Cl.
*H01L 21/00* (2006.01)

(52) U.S. Cl.
USPC .................. 438/49; 257/253; 257/E21.409

(58) Field of Classification Search
USPC ............... 257/252, 253, E21.409; 438/48, 49
See application file for complete search history.

(56) References Cited

U.S. PATENT DOCUMENTS

| | | | | |
|---|---|---|---|---|
| 4,411,741 A | * | 10/1983 | Janata ........................... | 257/253 |
| 4,773,970 A | * | 9/1988 | Purbrick et al. ............ | 205/778.5 |
| 4,839,000 A | * | 6/1989 | Eddowes ..................... | 205/778 |
| 4,878,015 A | * | 10/1989 | Schmidt et al. .............. | 324/71.5 |
| 4,894,339 A | * | 1/1990 | Hanazato et al. ............. | 435/182 |
| 6,794,805 B1 | * | 9/2004 | Hatai et al. ................... | 313/309 |
| 7,329,387 B2 | * | 2/2008 | Fukutani et al. ........... | 422/82.01 |
| 7,754,056 B2 | * | 7/2010 | Chou et al. ............... | 204/192.15 |
| 7,829,362 B2 | * | 11/2010 | Fukutani et al. ................ | 438/49 |
| 8,062,488 B2 | * | 11/2011 | Chou et al. ............... | 204/403.01 |
| 8,431,001 B2 | * | 4/2013 | Yu et al. ......................... | 204/416 |
| 2006/0163662 A1 | * | 7/2006 | Kinoshita et al. ............. | 257/369 |
| 2008/0014730 A1 | * | 1/2008 | Arghavani et al. ............ | 438/595 |
| 2011/0197657 A1 | * | 8/2011 | Gole ........................... | 73/31.05 |
| 2012/0055236 A1 | * | 3/2012 | Takulapalli .................. | 73/31.06 |
| 2012/0304741 A1 | * | 12/2012 | Roy et al. ..................... | 73/31.06 |

FOREIGN PATENT DOCUMENTS

| | | | | | |
|---|---|---|---|---|---|
| JP | H64-68650 | | * | 3/1989 | ............ G01N 27/00 |
| JP | H6-249824 | | * | 9/1994 | ............ G01N 27/414 |
| JP | 2002-250712 | | * | 9/2002 | ............ G01N 27/414 |
| JP | 2003-66000 | | * | 3/2003 | ............ G01N 27/414 |

OTHER PUBLICATIONS

JPO English summary, Hanasato, JP H64-68650 (1994), JPO and Japio, all pages.*

(Continued)

*Primary Examiner* — Fernando L Toledo
*Assistant Examiner* — Victoria K Hall
(74) *Attorney, Agent, or Firm* — Barry Choobin; Patent 360 LLC

(57) ABSTRACT

The various embodiments herein provide a method for fabricating Ion-Selective Field-Effect Transistor (ISFET) with a nano porous poly silicon layer on a gate region. The method includes providing a p-type silicon substrate and forming a silicon dioxide layer on the p-type silicon substrate. A poly silicon layer is deposited on the silicon dioxide layer. The poly silicon layer is patterned to form a gate region, a source region and a drain region in the silicon dioxide layer. A passivation layer is deposited on the gate region, source region and the drain region. The passivation layer is etched using a buffered HF to transform the poly silicon layer into a nano porous layer on the gate region by a sequential reactive ion etching process.

13 Claims, 24 Drawing Sheets

(56) References Cited

OTHER PUBLICATIONS

Machine translation, Arii, JP 2003-6600 (Apr. 5, 2013 translation by AIPN), all pages.*

Machine translation, Takada, JP H6-249824 (Apr. 5, 2013 translation by AIPN), all pages.*

Machine translation, Sakai, JP 2002-250712 (Apr. 5, 2013 translation by AIPN), all pages.*

Li et al., High-performance capacitive humidity sensor based on silicon nanoporous pillar array, Thin Solid Films, vol. 517, pp. 948-951 (published Jul. 24, 2008).*

Sammak et al., Deep Vertical Etching of Silicon Wafers Using Hydrogenation-Assisted Reactive Ion Etching, J. Microelectromechanical Sys., vol. 16, No. 5 (Aug. 2007), all pages.*

Ali et al., Porous silicon as substrate for ion sensors, Sensors & Actuators, vol. 74, pp. 123-125 (1999).*

Stewart et al., Chemical and Biological Applications of Porous Silicon Technology, Advanced Materials, vol. 12, No. 12 (2000), all pages.*

Translation, Hanazato, JP H64-068650, translation date: Apr. 2013, by The McElroy Translation Co., all pages.*

* cited by examiner

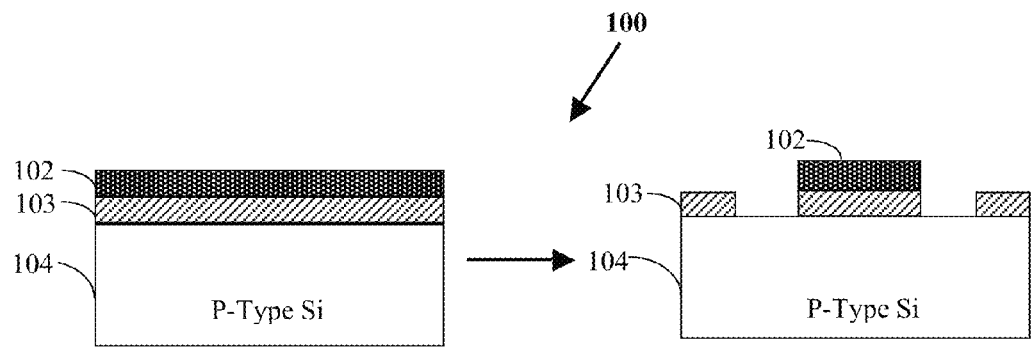
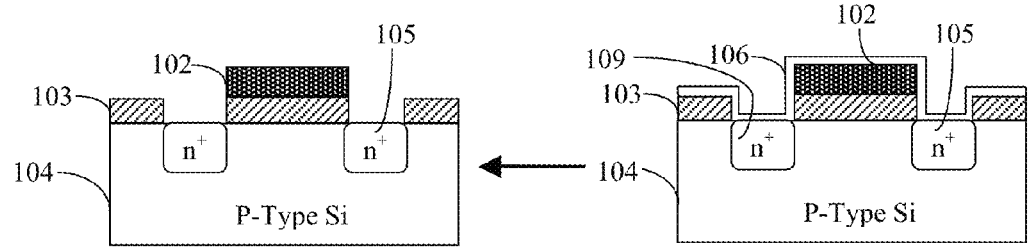
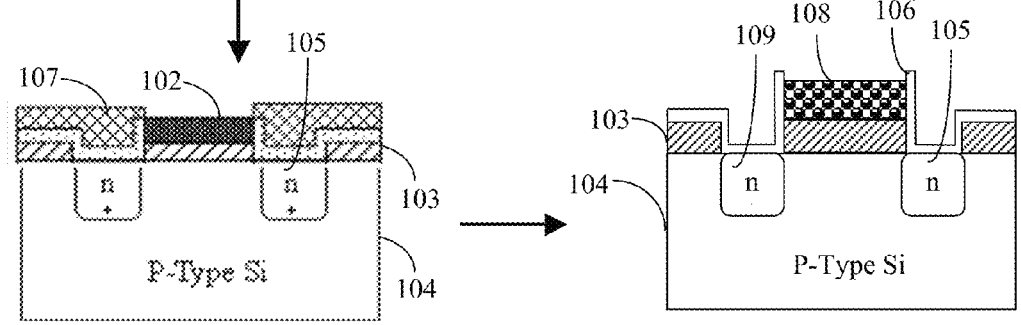
FIG. 1a FIG. 1b FIG. 1c FIG. 1d FIG. 1e FIG. 1f

METHOD AND SYSTEM FOR FABRICATING ION-SELECTIVE FIELD-EFFECT TRANSISTOR (ISFET)

This application claims the benefit of Provisional Application No. 61/472,283, filed on Apr. 6, 2011.

BACKGROUND

1. Technical Field

The embodiments herein generally relate to Ion-Selective Field-Effect Transistors (ISFET) and particularly relate to highly sensitivity nano-porous ISFET devices. The embodiments herein more particularly relate to a fabrication of a high Ph sensitive ISFETs and a method for fabricating a gate region of the ISFET with a nano porous layer.

2. Description of the Related Art

Ion selective field effect transistors (ISFET) are microelectronic products that have an important role in the development of chemical sensors. ISFET is analogous to MOSFET transistors where the metallic gate is replaced by a sensitive membrane and a reference electrode. The silicon dioxide surface contains reactive SiOH groups that can be used for covalent attachment of organic molecules and polymers. The various characteristics of the ISFET such as rapid response, low sample volumes and capabilities of on-chip circuit integration make the ISFET desirable for biosensor applications.

Currently the Ion selective field effect transistors (ISFET) are widely used as pH meters. The pH sensitivity of ISFETs is varied with respect to a transistor threshold voltage and is limited to values around 59 mv/pH according to Nernstian behaviour. The adsorbed charge layer on the sensitive membrane causes a shift in the threshold voltage due to the Nernst law.

In the existing techniques, the maximum achievable sensitivity of 59 mV/pH is relatively small when biological detection with ultra low concentration is required. Currently the low sensitivity problem is overcome by creating a porous layer on gate surface. The porous layer formed on the gate surface changes the electrical properties such as the electrical resistance or impedance.

Further, in the existing techniques, the porous structures are used for capacitance based devices and they show low sensitivity. In addition to the above, the porous sensors are not transistors. So there is no sign of amplification for such devices.

Hence there is a need to provide a method for fabricating ISFET through a formation of nano-porous structures of poly silicon films at active regions such as gate regions to realize high sensitivity pH transistors. There also exists a need to provide a method to integrate a nano-porous layer with active electronic components such as transistors.

The abovementioned shortcomings, disadvantages and problems are addressed herein and which will be understood by reading and studying the following specification.

OBJECTS OF THE EMBODIMENTS

The primary object of the embodiments herein is to provide a method for fabricating gate region of an Ion-Selective Field-Effect Transistor (ISFET) with a nano porous layer.

Another object of the embodiments herein is to provide a method for fabricating the ISFET with a nano-porous layer to increase the effective adsorption surface of the ISFETs.

Yet another object of the embodiments herein is to provide a method for fabricating the ISFET with a nano-porous layer to make the nano-porous ISFET devices with an ultra high sensitivity due to a non-linear behavior.

Yet another object of the embodiments herein is to provide a method for fabricating the ISFET with a nano-porous layer adapted to act as an acceptor of biological objects when a physical adsorption is required.

Yet another object of the embodiments herein is to provide a method for fabricating the ISFET with a nano-porous layer to enhance the stabilization of one or more acceptors when a chemical adsorption is required.

Yet another object of the embodiments herein is to provide a method for fabricating the ISFET with a nano-porous layer to integrate porous semiconductors with a plurality of active electronic components such as transistors.

Yet another object of the embodiments herein is to provide a method for fabricating the ISFET with a nano-porous layer to increase the threshold voltage response to sensor's input.

Yet another object of the embodiments herein is to provide a method for fabricating the ISFET with a nano-porous layer to increase the variation of a slope in the electrical drain-voltage characteristics.

These and other objects and advantages of the embodiments herein will become readily apparent from the following detailed description taken in conjunction with the accompanying drawings.

SUMMARY

The embodiments herein provide a method for fabricating an Ion-Selective Field-Effect Transistor (ISFET). The method involves providing a p-type silicon substrate and forming a silicon dioxide layer on the p-type silicon substrate. The method further includes depositing a poly silicon layer on the silicon dioxide layer formed on the p-type silicon substrate. The method includes patterning the poly silicon layer deposited on the silicon dioxide layer as a gate region and forming a source region and a drain region in the silicon dioxide layer. The method further includes depositing a passivation layer on the gate region, source region and the drain region formed in the p-type silicon substrate. The method also includes etching the passivation layer deposited on the patterned poly silicon layer using a buffered HF and transforming the poly silicon layer into a nano porous layer on the gate region of the p-type silicon substrate by a sequential reactive ion etching process.

According to an embodiment herein, the source region and the drain region is defined by performing a diffusion of the silicon dioxide layer at a temperature of 800° C.

According to an embodiment herein, the passivation layer deposited on the patterned poly silicon layer is etched using a sequential reactive ion etching process.

According to an embodiment herein, the silicon dioxide layer is formed on the p-type substrate with a thickness of 120 nm.

According to an embodiment herein, the poly silicon layer is deposited on the silicon dioxide layer with a thickness of 1.5 µm.

According to an embodiment herein, the poly silicon layer is deposited on the silicon dioxide layer using a low-pressure chemical-vapor-deposition process.

According to an embodiment herein, the passivation layer deposited on the patterned poly silicon layer is a trilayer with a thickness of 1.3 µm and the passivation layer is deposited on the surface of the poly silicon layer.

According to an embodiment herein, the passivation layer deposited on the sensor is a SiOxNy layer with a thickness of 1.3 μm and the passivation layer deposited on the surface of the poly silicon layer is removed for texturing the gate region According to an embodiment herein, the passivation layer deposited on the patterned poly silicon layer is etched away based on the dimensions of the poly silicon gate region.

According to an embodiment herein, the poly silicon layer is transformed into a nano-porous layer by passivating the poly silicon layer with plasma containing a mixture of $H_2/O_2$ gases having a trace amount of $SF_6$ and etching the poly silicon layer using $SF_6$ as an inlet gas.

According to an embodiment herein, the nano porous layer formed on the gate region of the p-type substrate transmits an ion effect to the underlying silicon dioxide layer.

According to an embodiment herein, the etching of the passivation layer deposited on the patterned poly silicon layer involves applying a mask of photo resist on the source region and the drain region defined.

According to an embodiment herein, the nano porous layer is formed on the gate region through a hydrogen-assisted dry etching process.

According to an embodiment herein, the nano porous layer formed on the gate region is adapted to function as an acceptor of biological objects when a physical adsorption is required.

According to an embodiment herein, the nano porous layer formed on the gate region is adapted to enhance the stabilization of one or more acceptors when a chemical adsorption is required.

According to an embodiment herein, the nano porous layer formed on the gate is adapted to integrate porous semiconductors with a plurality of active electronic components.

According to an embodiment herein, the nano porous layer formed on the gate region is made of nano porous silicon.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which:

FIG. 1a-1f illustrate a schematic side sectional view of fabricating a gate region of an Ion-Selective Field-Effect Transistor (ISFET) with a nano porous layer, according to one embodiment herein.

Figure 2:
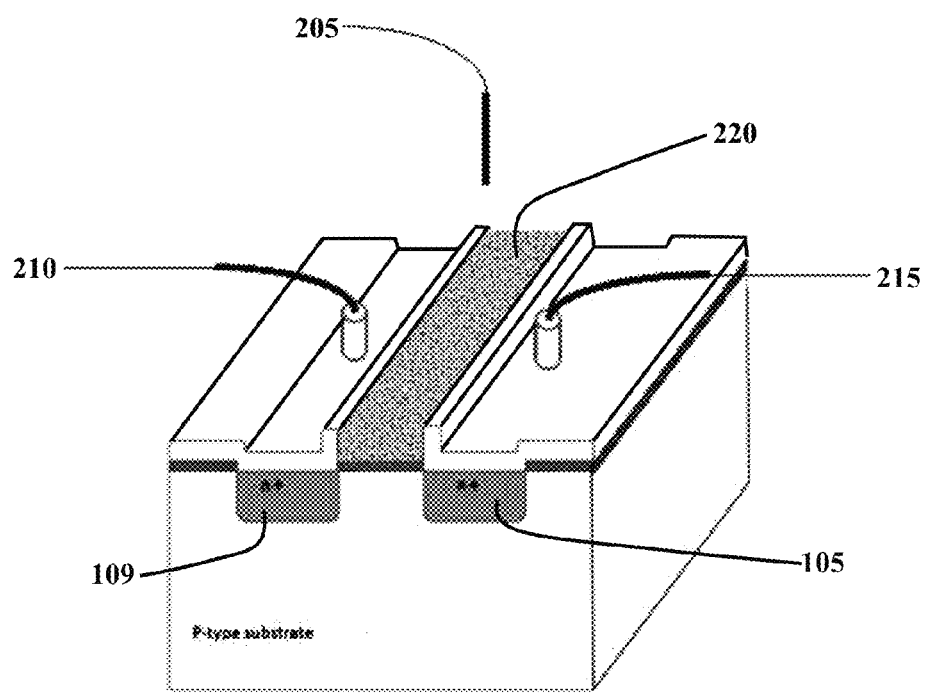
FIG. 2 illustrates a perspective view of an Ion-Selective Field-Effect Transistor (ISFET), according to one embodiment herein.

Although the specific features of the embodiments herein are shown in some drawings and not in others, this is done for convenience only as each feature may be combined with any or all of the other features in accordance with the embodiment herein.

DETAILED DESCRIPTION OF THE EMBODIMENTS

In the following detailed description, a reference is made to the accompanying drawings that form a part hereof, and in which the specific embodiments that may be practiced is shown by way of illustration. These embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The embodiments herein provide a method for fabricating an Ion-Selective Field-Effect Transistor (ISFET). The method involves providing a p-type silicon substrate and forming a silicon dioxide layer on the p-type silicon substrate. A poly silicon layer is deposited on the silicon dioxide layer formed on the p-type substrate. The poly silicon layer deposited on the silicon dioxide layer is patterned to form a gate region, a source region and a drain region in the silicon dioxide layer. A passivation layer is deposited on the gate region, source region and the drain region formed in the p-type silicon substrate. The passivation layer deposited on the patterned poly silicon layer is etched using a buffered HF and the poly silicon layer is transformed into a nano porous layer on the gate region of the p-type silicon substrate by using a sequential reactive ion etching process.

The source region and the drain region are defined by performing a diffusion of the silicon dioxide layer at a temperature of 800° C.

The passivation layer deposited on the patterned poly silicon layer is etched using a sequential reactive ion etching process.

The silicon dioxide layer formed on the p-type substrate is 120 nm in thickness.

The poly silicon layer deposited on the silicon dioxide layer is 1.5 μm in thickness.

The poly silicon layer is deposited on the silicon dioxide layer using a low-pressure chemical-vapor-deposition process.

The passivation layer deposited on the patterned poly silicon layer is a silicon-oxy-nitride layer with a thickness of 1.3 μm on the surface of the poly silicon layer.

The passivation layer deposited on the patterned poly silicon layer is etched based on the width and length of gate channel.

The nano porous layer formed on the gate region of the p-type substrate transmits an ion effect to the underlying silicon dioxide layer.

The etching of the passivation layer deposited on the patterned poly silicon layer involves applying a mask of photo resist on the source region and the drain region defined.

The nano porous layer is formed on the gate region through a hydrogen-assisted dry etching process.

The nano porous layer formed on the gate region is adapted to function as an acceptor of biological objects when a physical adsorption is required.

The nano porous layer formed on the gate region is adapted to enhance the stabilization of one or more acceptors when a chemical adsorption is required.

The nano porous layer formed on the gate is adapted to integrate the porous semiconductors with a plurality of active electronic components.

The nano porous layer formed on the gate region is made of nano porous silicon.

FIG. 1a-1f illustrates the schematic side sectional views of an ion-selective field-effect transistor during a fabricating of a gate region in an ion-selective field-effect transistor (ISFET) with a nano porous layer, according to one embodiment herein. With respect to FIG. 1a-1f, the ion-selective field-effect transistor (ISFET) 100 is fabricated using N-MOS transistors on P-type silicon wafers or p type Si substrate 104. A silicon dioxide layer 103 is deposited on the p-type silicon substrate 104. A thermally grown silicon dioxide layer 103 is used as the gate dielectric material where its thickness is 120 nm. A poly silicon layer 102 formed on the p-type substrate 104. The initial thickness of the poly silicon layer 102 is set about 1 μm in thickness. The source and drain regions 105, 109 are then defined using a diffusion process at a temperature of 800 degree Celsius. A passivation layer 106 is deposited on the patterned poly silicon layer. A layer of SiOxNy deposited using a pressure chemical-vapour-deposition (PECVD) process passivates the whole structure of the ISFET. A mask of photo resist 107 is applied on the source region and the drain region defined. The passivation layer 106 deposited on the patterned poly silicon layer is then etched. The passivation layer 106 on the gate poly silicon film is etched away by means of buffered-HF. The poly silicon layer is then transformed into a nano porous layer 108 on the gate region of the p-type silicon substrate by using a reactive ion etching process. The passivation layer deposited on the patterned poly silicon layer is a silicon-oxy-nitride layer with a thickness of 1.3 μm on the surface of the poly silicon layer.

The reactive ion etching process includes two or three sub-cycles operated at 13.56 MHz. The reactive ion etching process is performed based on the repetition of two main steps such as etching and passivation processes. In the first sub-cycle of the reactive ion etching process, a mixture of $H_2$ and $SF_6$ gases respectively with a flow rate of 100 and 10 sccm is used while the plasma power is set at 250 W. The second sub-cycle is obtained using a mixture of $O_2$ and SF6 gases with a flow rate of 100 sccm and a plasma power of 200 W and 130 W. In the third sub-cycle $H_2/O_2$ gases are used. See Table 1.

FIG. 2 illustrates a perspective view of an Ion-Selective Field-Effect Transistor (ISFET), according to one embodiment herein. With respect to FIG. 2, the Ion-Selective Field-Effect Transistor (ISFET) is fabricated using N-MOS transistors on P-type oriented silicon wafers or p-type substrate. The Ion-Selective Field-Effect Transistor (ISFET) includes a reference electrode 205, a drain region 109 with a drain electrode 210, a source region 105 with a source electrode 215 and a porous gate region 220. The source region 105 and the drain region 109 are defined by performing a diffusion of the silicon dioxide layer at a temperature of 800° C. The nano porous layer formed on the gate region 220 of the p-type substrate transmits an ion effect to the underlying silicon dioxide layer. The nano porous layer is formed on the gate region 220 through a hydrogen-assisted dry etching process. The nano porous layer formed on the gate region 220 is adapted to function as an acceptor of biological objects when a physical adsorption is required. Further the nano porous layer formed on the gate region 220 is adapted to integrate porous semiconductors with a plurality of active electronic components.

Figure 3:
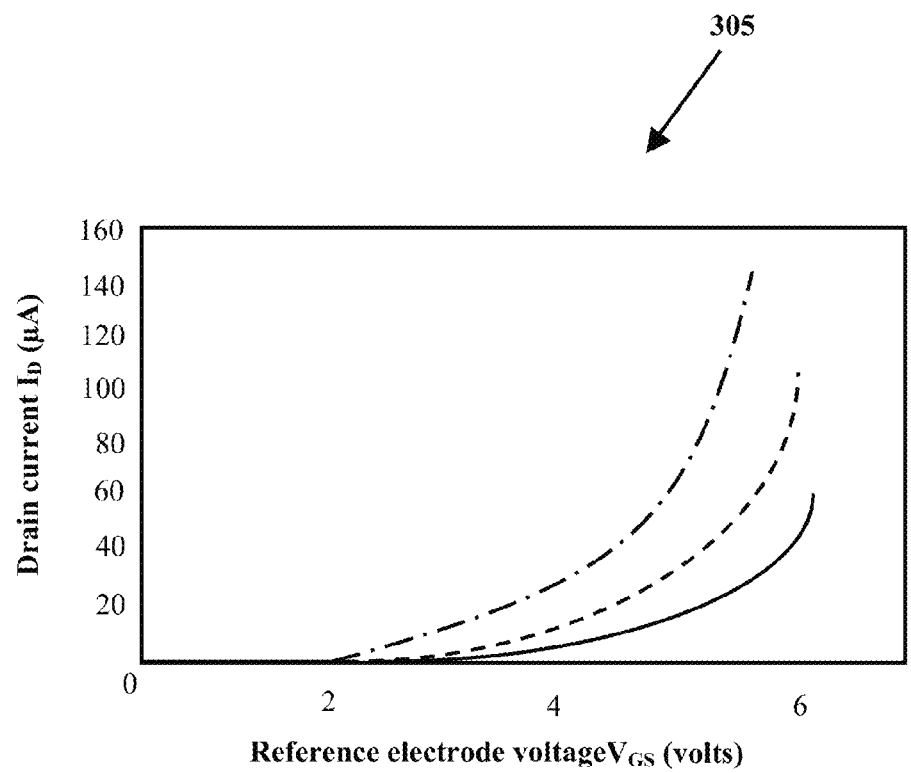
FIG. 3 illustrates a graph indicating slope variation of the current characteristic of an Ion-Selective Field-Effect Transistor (ISFET), for different solutions with varying pH from 4 to 9, according to one embodiment herein.

FIG. 3 illustrates a graph indicating a slope variation evidencing a significant increase in the transistor current in the Ion-Selective Field-Effect Transistor (ISFET), according to one embodiment herein. With respect to FIG. 3, a graph 305 is plotted for a regular ISFET-pH meter fabricated under current bias conditions. Further the graph 305 is plotted with the drain current $I_D$ as the y axis and the gate-source voltage $V_{GS}$ as the x-axis. The sensitivity is defined as the shift in the $I_D$-$V_{GS}$ characteristics for different pH values of solutions. As a result of changes in the slope of $I_D$-$V_{GS}$ curves, a higher current biases lead to higher sensitivities.

Figure 4:
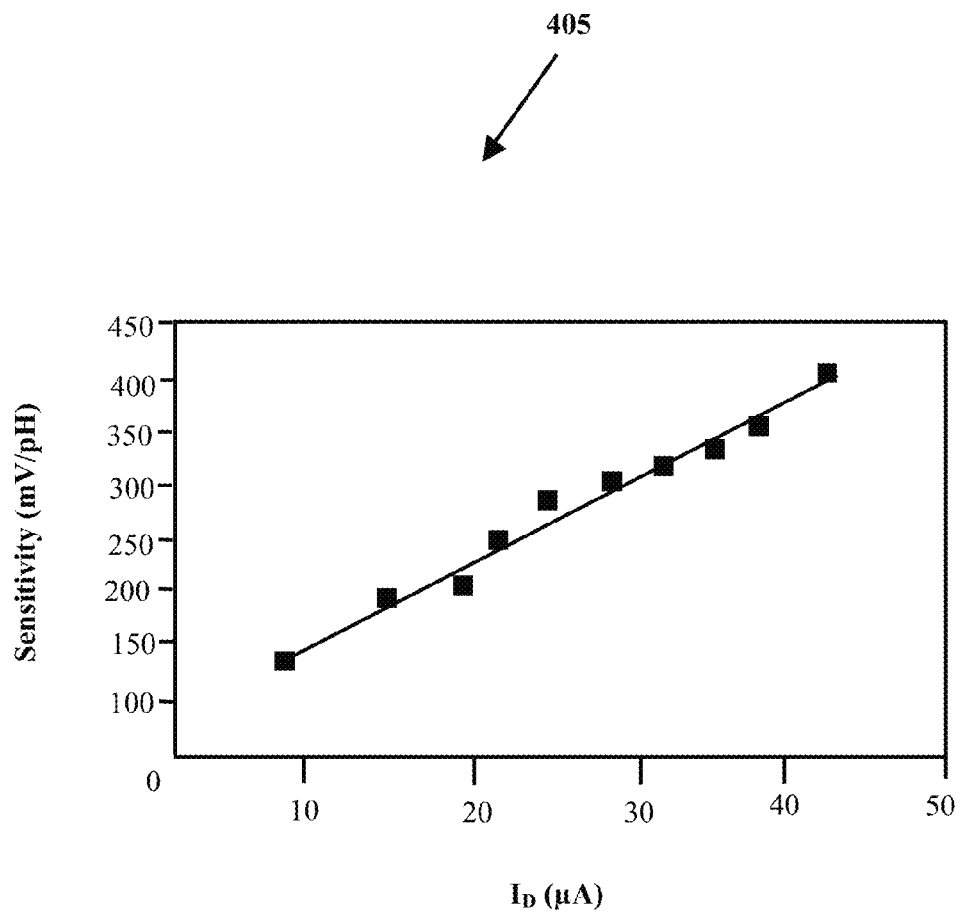
FIG. 4 illustrates a graph indicating a constant current sensitivity for an ISFET under different current bias conditions, according to one embodiment herein.

FIG. 4 illustrates a graph of constant current sensitivity for a fabricated ISFET under different current bias conditions, according to one embodiment herein. With respect to FIG. 4, a graph 405 is plotted with constant current sensitivity for a fabricated ISFET under different current bias conditions. The current characteristics shift is not significant and the ISFET device shows a non-linear performance. The presence of the nano-structured poly silicon film on the gate region results in effective gate voltage being modulated significantly by the pH value. The response of such fabricated ISFET transistors to pH value is different from normal ISFETs which the change in the threshold voltage is recorded with respect to Nernstian behaviour.

The FIG. 4 represents sensitivity for different drain current biases. As shown in FIG. 4, the sensitivity 150 to 400 mv/pH is obtainable. Further, based on constant transistor current definition of sensitivity, a high shift in the gate-source voltage up to 500 m V/pH is observable.

Figure 5A:
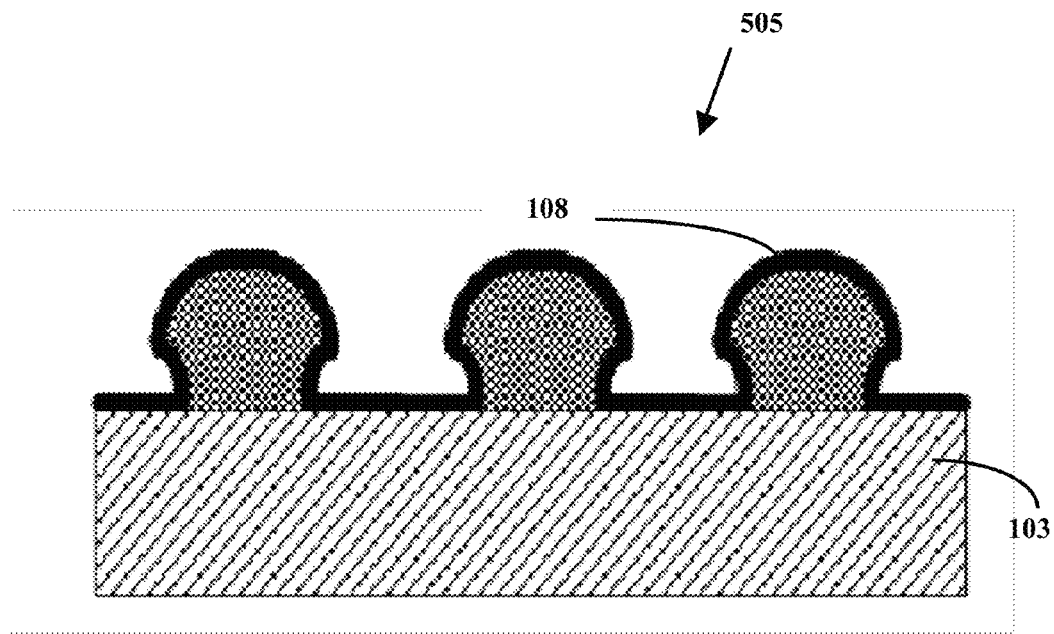
FIG. 5a and FIG. 5b illustrate schematic side sectional views of a porous surface and a planar surface formed on an active region in an Ion-Selective Field-Effect Transistor (ISFET), according to one embodiment herein.
Figure 5B:
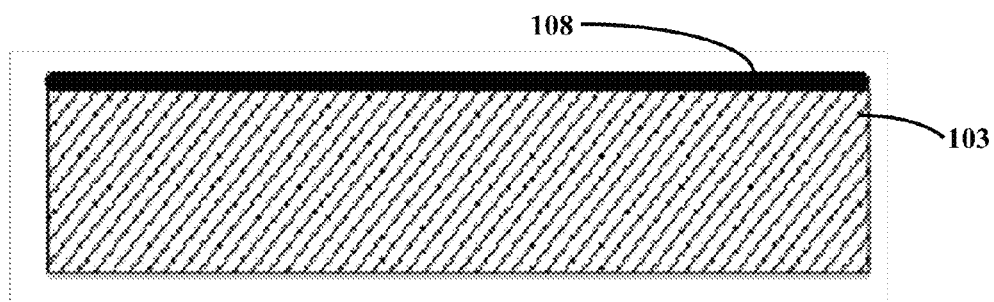

FIG. 5a and FIG. 5b illustrate a side sectional view of a porous surface and a planar surface 505 formed from fabricating an Ion-Selective Field-Effect Transistor (ISFET), according to one embodiment herein. With respect to FIG. 5a, the porous surface 108 and the planar surface 505 increases the effective area of the ISFETs due to the porosity. The porous structures have higher adsorption surface and the nano porous poly silicon gate field effect transistor is used to increase the effective adsorption surface of the ISFETs. The nano porous layer is formed on the silicon dioxide layer 103 at the gate region through a hydrogen-assisted method. The nano porous layer is adapted to function as an acceptor of biological objects when physical and chemical adsorption is required. The nano porous layer formed on the gate region is made of nano porous silicon. The different size and shape of nano porous features might be critical in biological applications such as an enzyme or DNA detection.

Figure 6A:
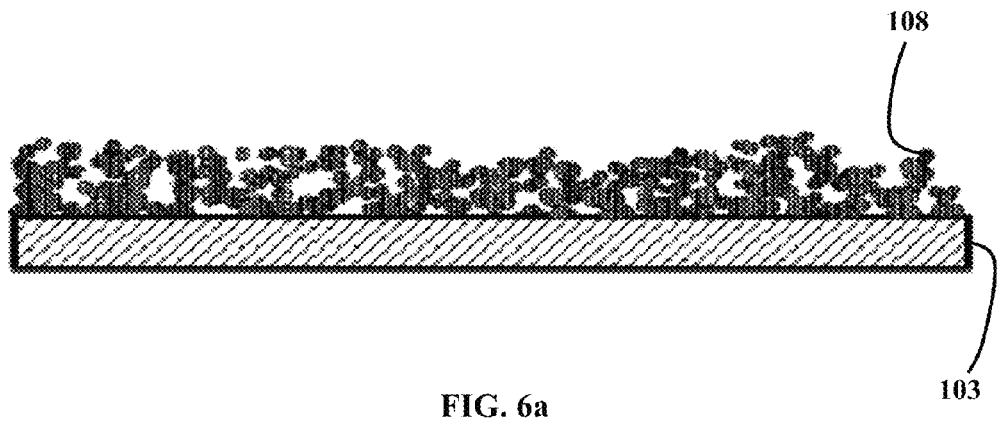
FIG. 6a and FIG. 6b illustrate schematic side sectional views of nano-porous structures formed on the gate region of the p-type silicon substrate by a reactive ion etching process in an Ion-Selective Field-Effect Transistor (ISFET), according to one embodiment herein.
Figure 6B:
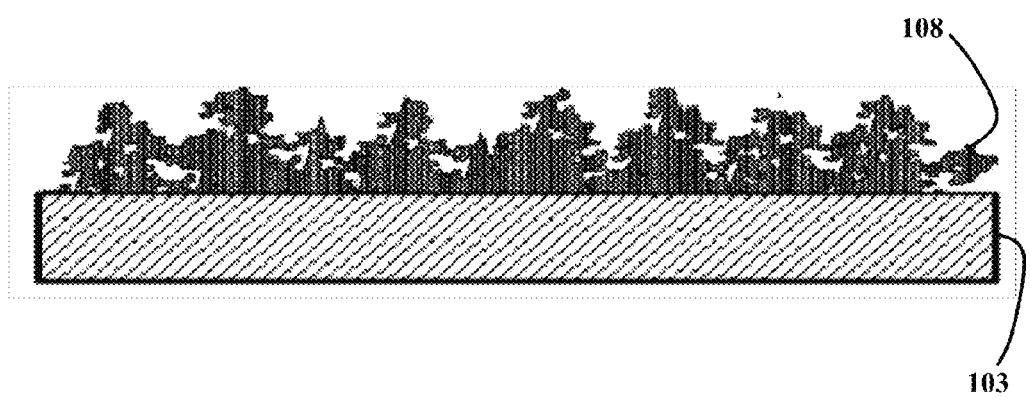
Figure 7A:
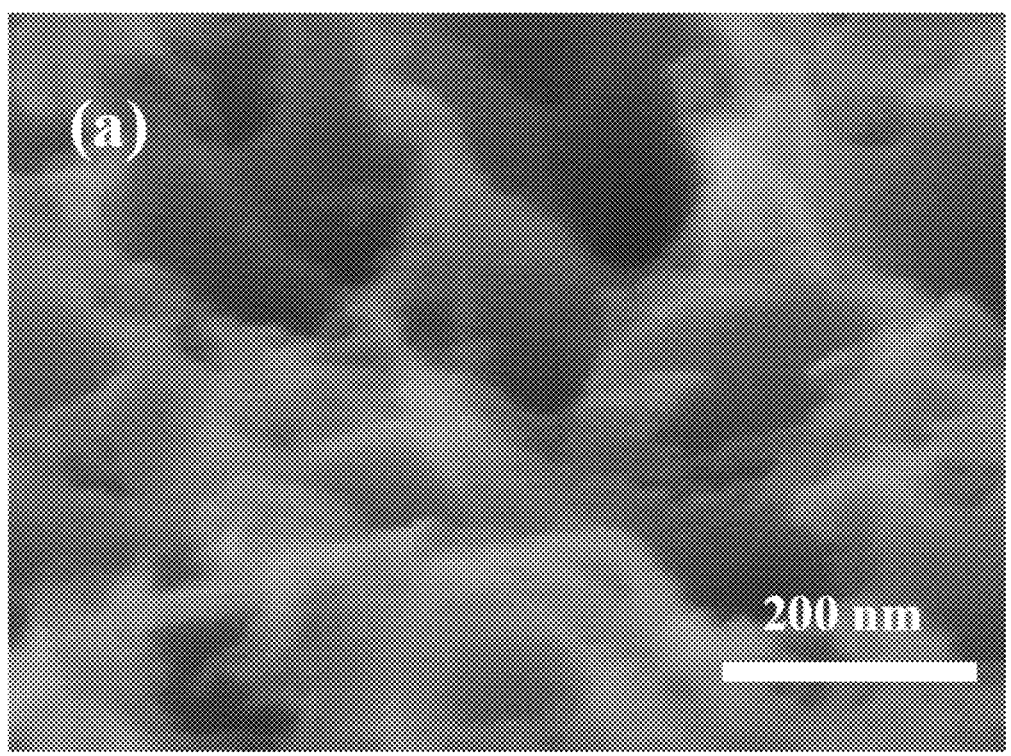
FIG. 7a-7d illustrate SEM images of nano-porous structure achieved by modification in etching process in an Ion-Selective Field-Effect Transistor (ISFET), according to one embodiment herein.
Figure 7B:
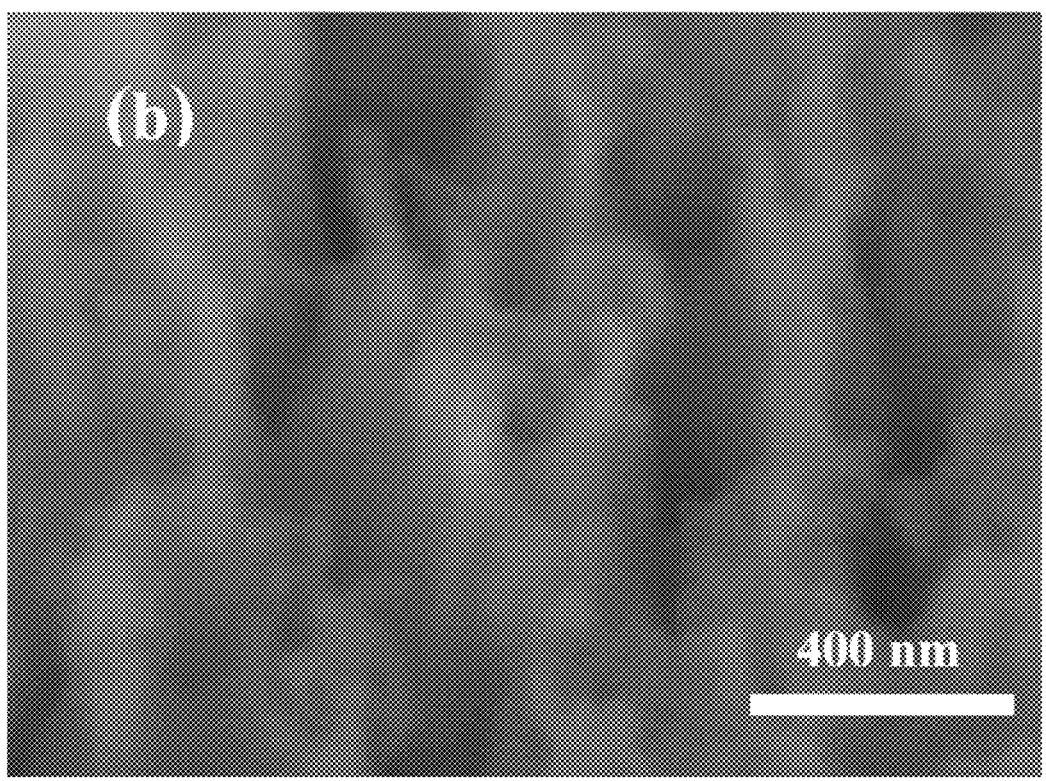
Figure 7C:
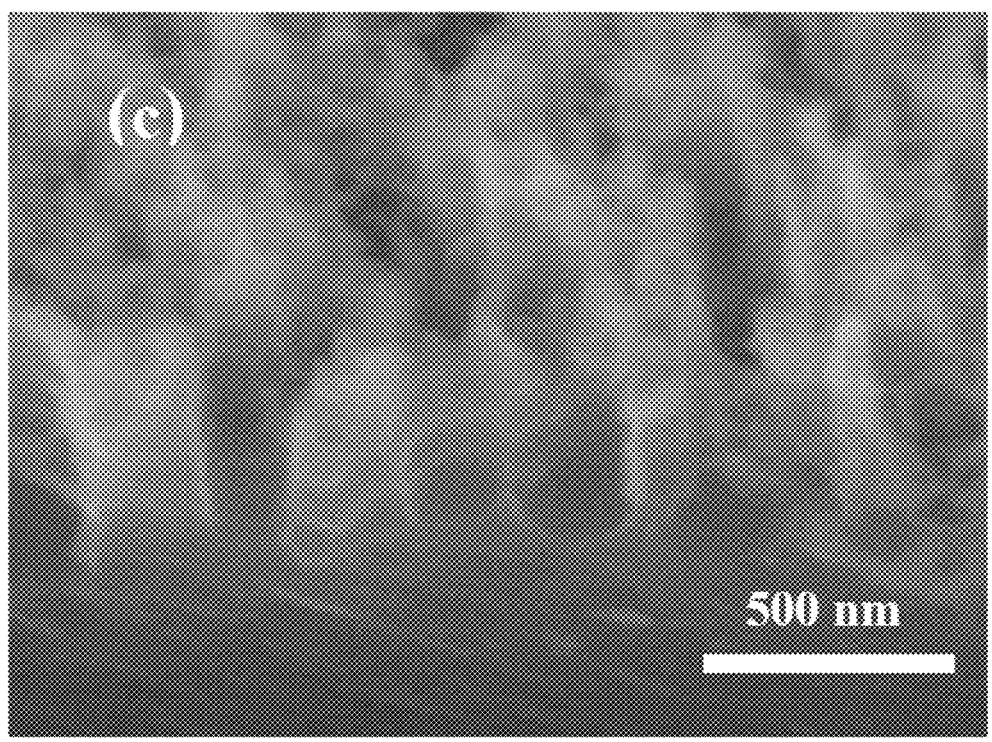
Figure 7D:
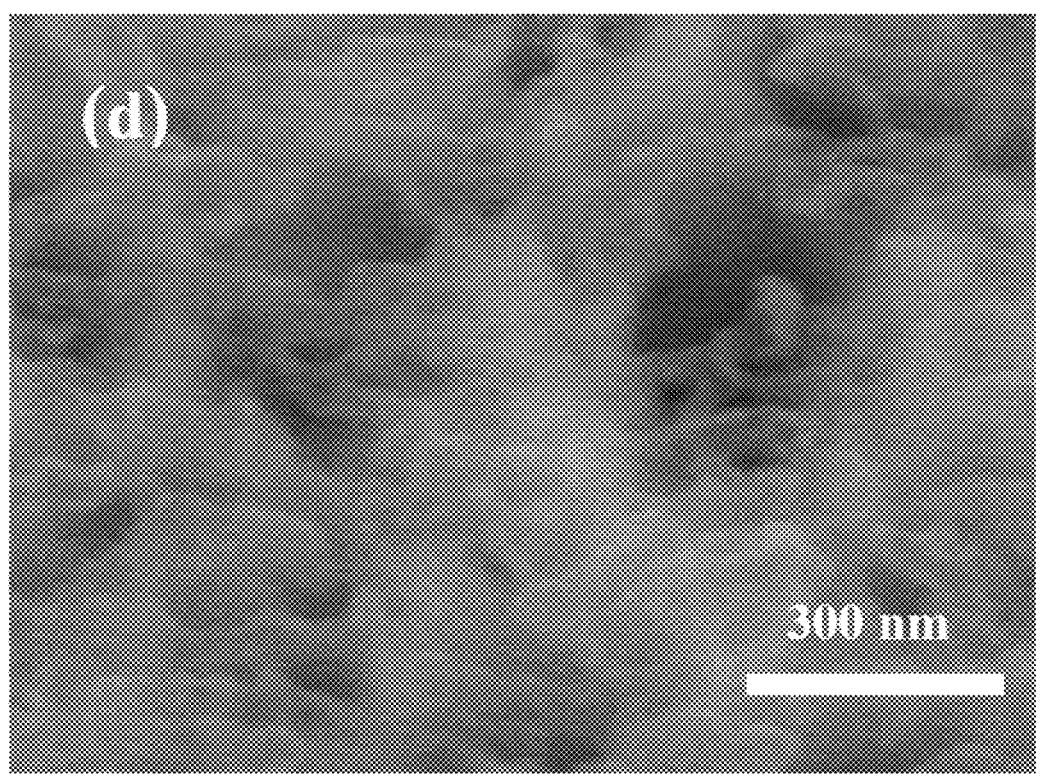

FIG. 6a and FIG. 6b illustrate a schematic view of nano-porous structures formed on the gate region of the p-type silicon substrate by reactive ion etching process, according to one embodiment herein. With respect to FIG. 6a, the nano-porous structures 108 are formed on the silicon dioxide layer 103 at the gate region of the p-type silicon-oxide substrate by the reactive ion etching process. As shown, the nano-porous structures 108 have the higher adsorption surface in comparison with planar surface shown in FIG. 6b. The incorporation of nano porous layers onto the gate region of field effect transistors results in achieving high sensitivity for the nano porous ISFET devices. The reactive ion etching process includes two or three sub cycles operated at 13.56 MHz. The reactive ion etching process is based on the repetition of two main steps of etching and passivation. In the first sub-cycle of the reactive ion etching process, a mixture of $H_2$ and $SF_6$ gases with respective flows of 100 sccm and 10 sccm are used while the plasma power is set at 250 W. The second sub-cycle is obtained using a mixture of $O_2$ and $SF_6$ gases with flows of 100 sccm and 0 sccm and plasma power of 200 W. In the third sub-cycle, $SF_6$ and $H_2/O_2$ gases are used with flows of 100 sccm and 0 sccm and a plasma power of 130 W.

The table given below provides information pertaining to the details of the gas flows, time, and plasma power used in the reactive ion etching process. The flow rate of hydrogen in the last sub-cycle is the main variable parameter in the reactive ion etching process. The variable parameter hydrogen mainly controls the etch rate and the desired feature sizes. The reactive ion etching process includes three sub-cycles and the process of fabricating porous poly-silicon is given below in the table.

TABLE 1

| Sub-cycle No. | Gas Type | Gas Flow (SCCM) | Plasma Power(Watt) & Etch Time(Second) |
|---|---|---|---|
| 1 | O2 | 0 | 250 Watt |
|  | SF6 | 10 | 90 s |
|  | H2 | 100 |  |
| 2 | O2 | 100 | 200 Watt |
|  | SF6 | 0 | 10 s |
|  | H2 | 0 |  |
| 3 | O2 | 0 | 130 Watt |
|  | SF6 | 100 | 10 s |
|  | H2 | Variable(0-10) |  |

FIG. 7a-7d illustrates SEM images of the nano-porous structures achieved by modification in the etching process, according to one embodiment herein. With respect to FIG. 7a-7d, is shown that the pores in the nano-porous structures are formed in the order of 50 nm by modifying the reactive ion etching process. The reactive ion etching process includes two or three sub-cycles operated at 13.56 MHz. The reactive ion etching process is based on the repetition of two main steps of etching and passivation. FIG. 7a-7d illustrates several SEM images of the nano-porous polysilicon structures on an oxide layer at different magnifications, indicating the formation of porous features, which have reached the bottom of the polysilicon layer. Different size and shape of nanoporous features might be critical in biological applications such as Enzyme or DNA detection. The difference between structure shapes in parts (a) to (d) of FIG. 7 is the result of the small modification in the etch-process. The $H_2$ presence in some sequences can decrease the etch rate and as a result, finer structures are achieved. This effect is observed in part (d) of FIG. 7.

Figure 8A:
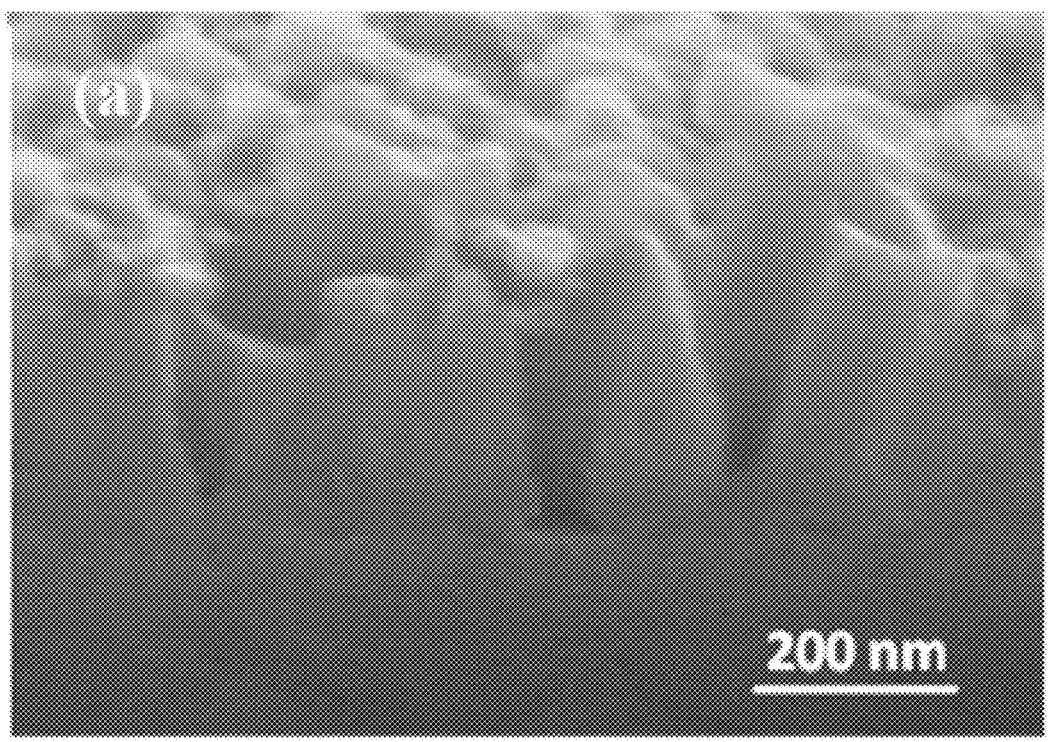
FIG. 8a-8c illustrate a cross section view of poly-Si etched partially, in the active region in an Ion-Selective Field-Effect Transistor (ISFET) according to one embodiment herein.
Figure 8B:
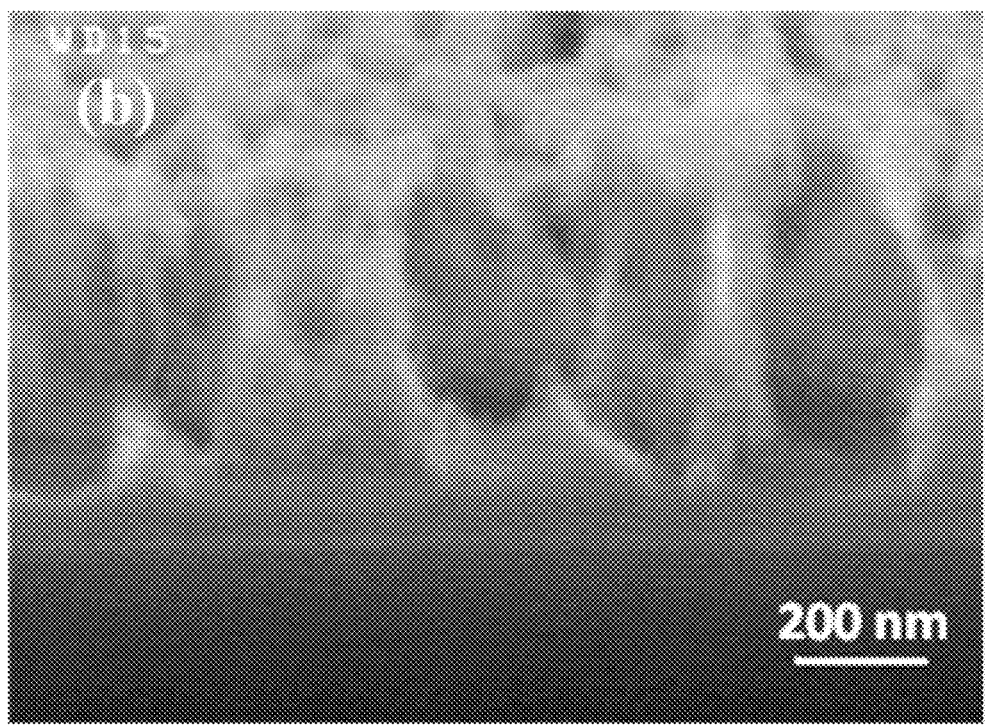
Figure 8C:
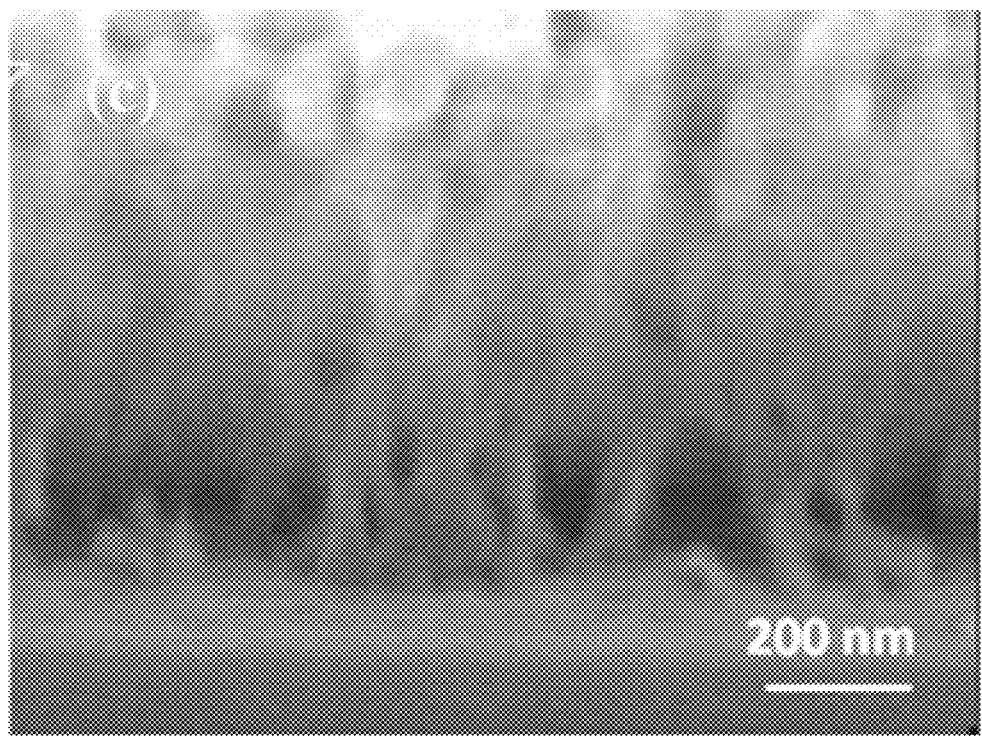

FIG. 8a-8c illustrates a cross sectional view of poly-Si etched partially, according to one embodiment herein. With respect to FIG. 8a-8c, the poly-Si is etched partially and the uniformity of the etch process in depth of all regions is maintained. The samples with the etching continued to oxide surface are shown in FIG. 8b-8c. The underlying oxide layer acts as etch stop and remains without any change in the surface. The etching process in the poly-Si layer has progressed uniformly from top to bottom as observed in this figure. In part (c) of FIG. 8, one can see a highly porous nano-structured silicon film on an oxide layer where pores of the size of 20-50 nm are observed. A Hitachi SE-4160 field emission scanning electron microscope has been used to investigate the nano-porous formation.

Figure 9A:
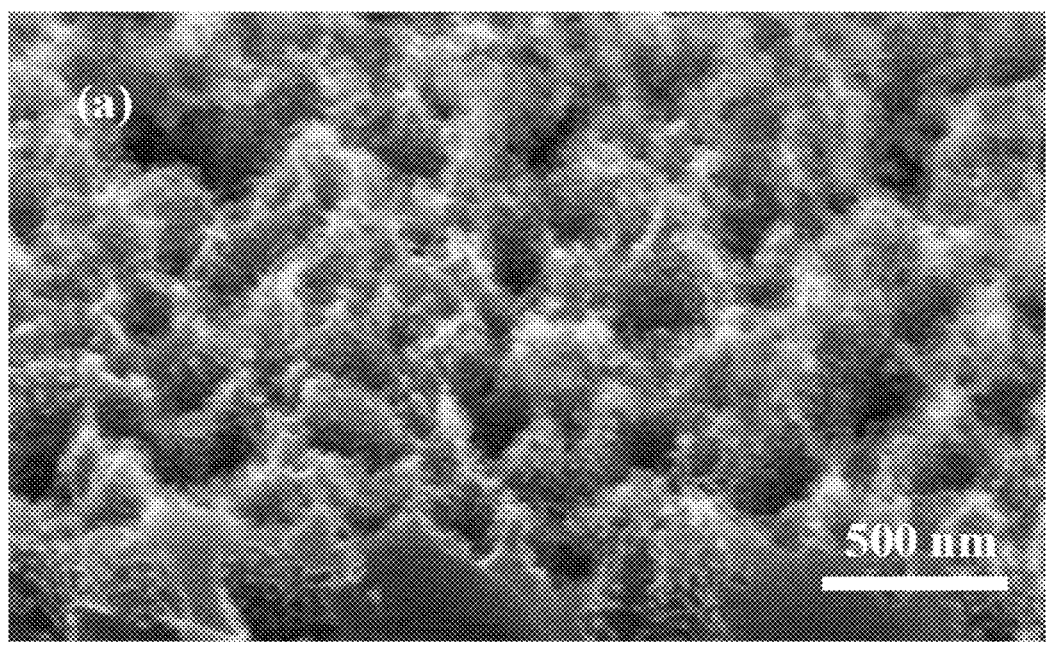
FIG. 9a-9b illustrate a cross section view of poly-Si etched after thermal annealing in Ar right before etching, in an ion-Selective Field-Effect Transistor (ISFET) according to one embodiment herein.
Figure 9B:
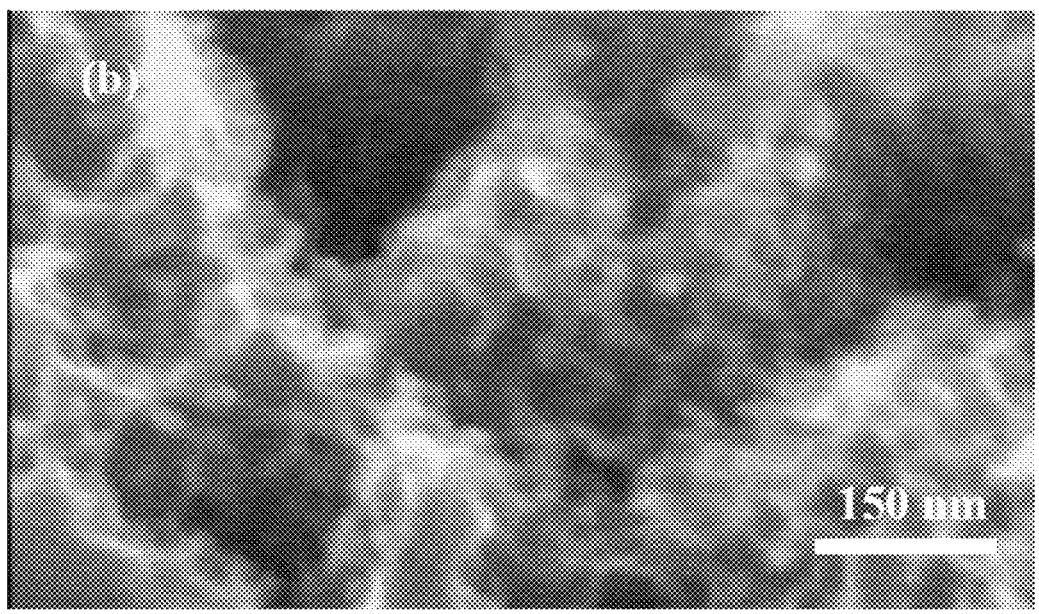

FIG. 9a-9b illustrates a cross sectional view of poly-Si annealed in Ar just before etching, according to one embodiment herein. With respect to FIG. 9a-9b, the results of the reactive ion etching process performed on the annealed poly-silicon layer using Ar at 850° C. just prior to RIE process are shown with different magnifications. The cross sectional view shows the different magnifications of poly-Si etched using RIE process.

Figure 10A:
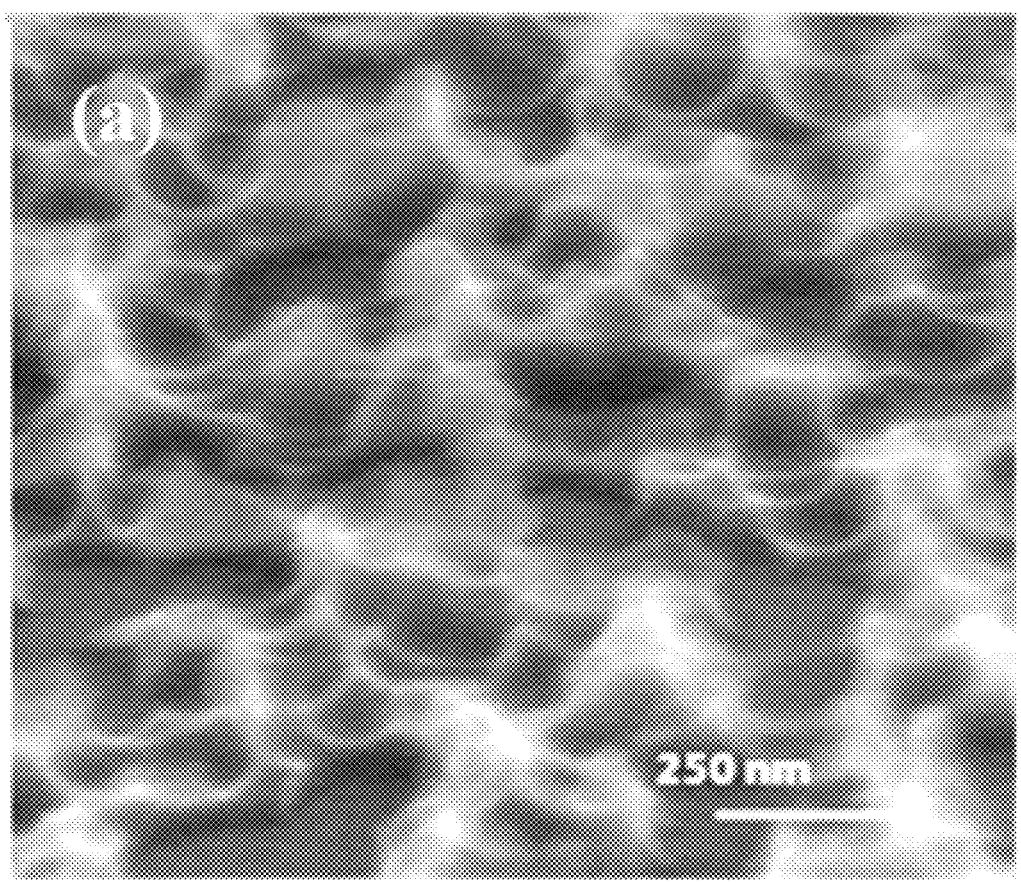
FIG. 10a-10c illustrate a cross section view of various samples annealed using RIE process during a fabrication of an Ion-Selective Field-Effect Transistor (ISFET), according to one embodiment herein.
Figure 10B:
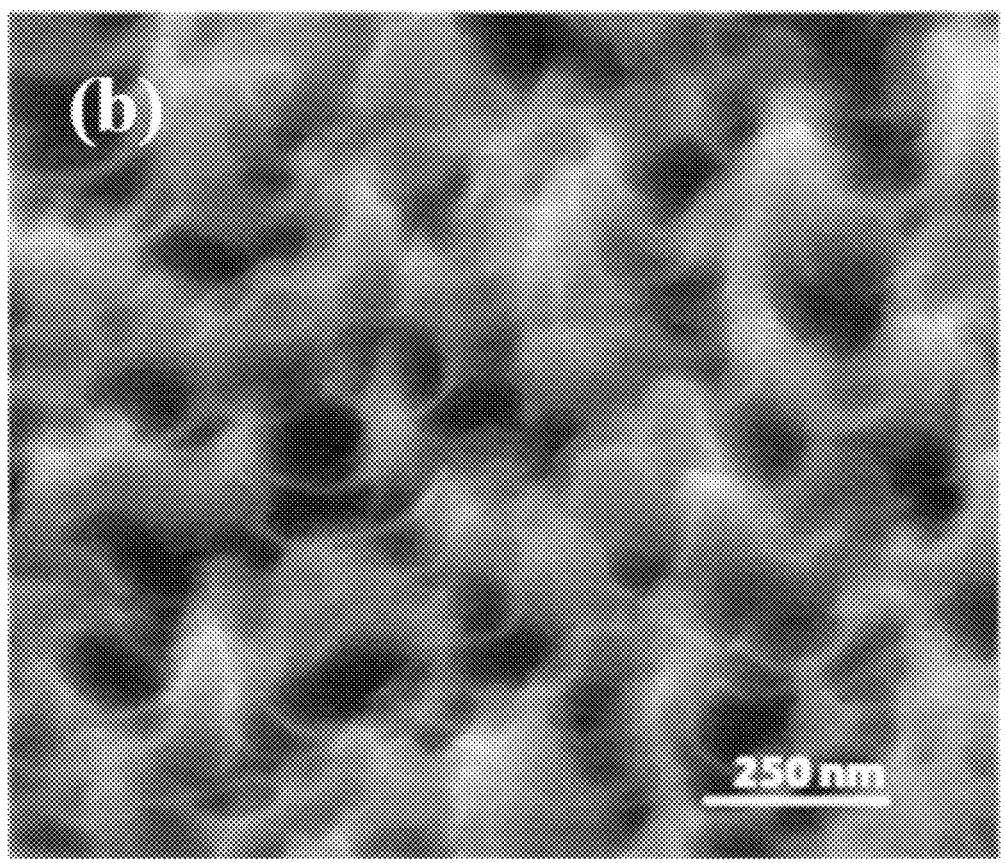
Figure 10C:
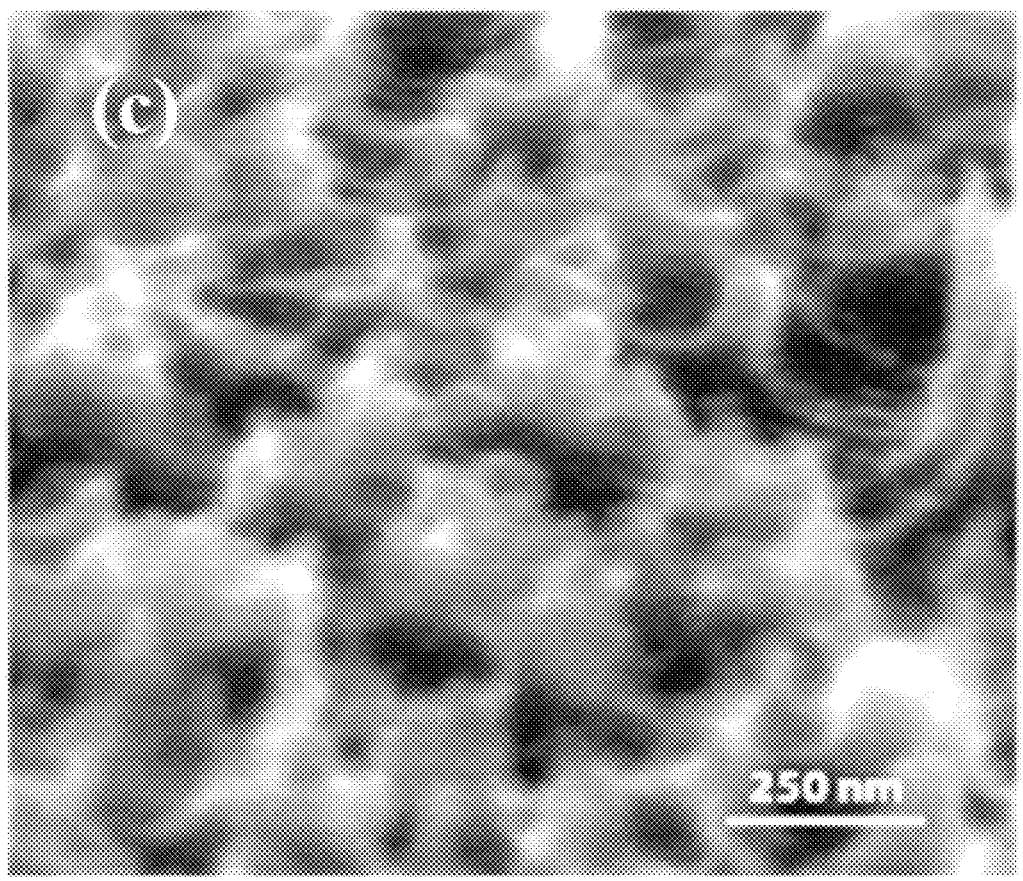

FIG. 10a-10c illustrates a cross sectional view of various samples annealed using RIE process, according to one embodiment herein. With respect to FIG. 10a-10c, the effect of the RIE process with various samples annealed at 300° C., 700° C. and 900° C. are shown in the FIG. 10a-10c. The higher temperature treatment leads to more resistance in the etching step, hence achieving finer nano porous structures.

Figure 11A:
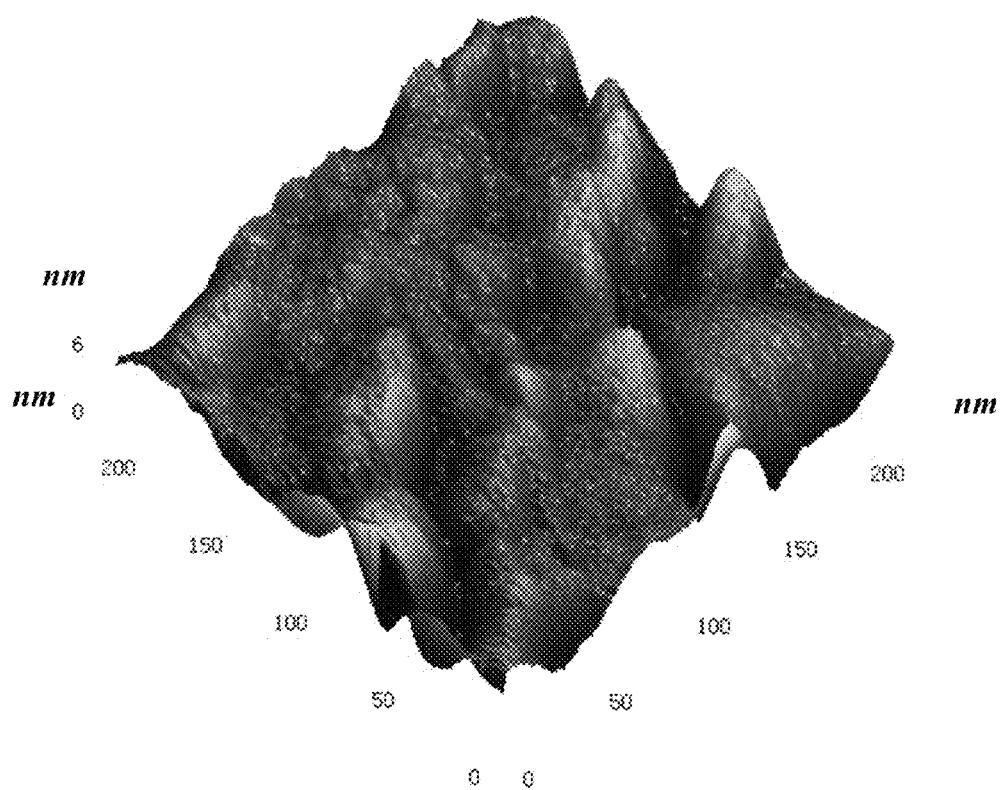
FIG. 11a-11b illustrate the AFM images of the nano-porous surface in an active region in an Ion-Selective Field-Effect Transistor (ISFET) according to one embodiment herein.
Figure 11B:
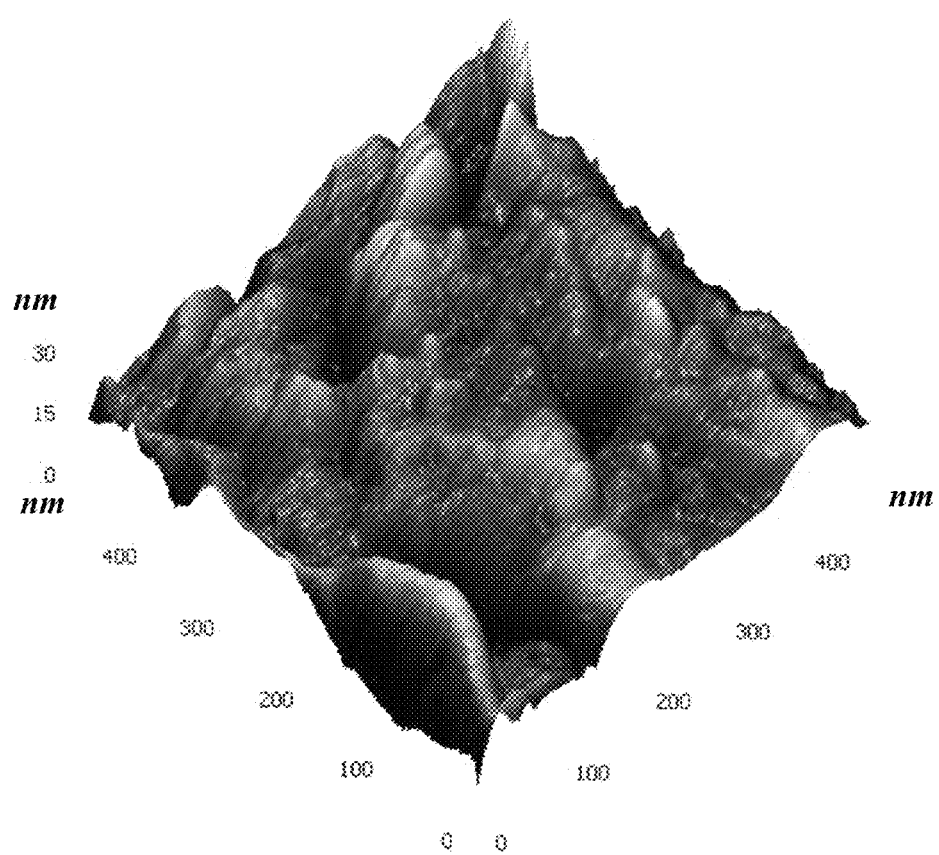

FIG. 11a-11b illustrates the AFM images of the nano-porous surface, according to one embodiment herein. With respect to FIG. 11a-11b, the nano-porous structures are formed on the gate region of the p-type silicon substrate by reactive ion etching process. The incorporation of nano porous layers onto the gate region of field effect transistors results in achieving high sensitivity for the nano porous ISFET devices.

Figure 12A:
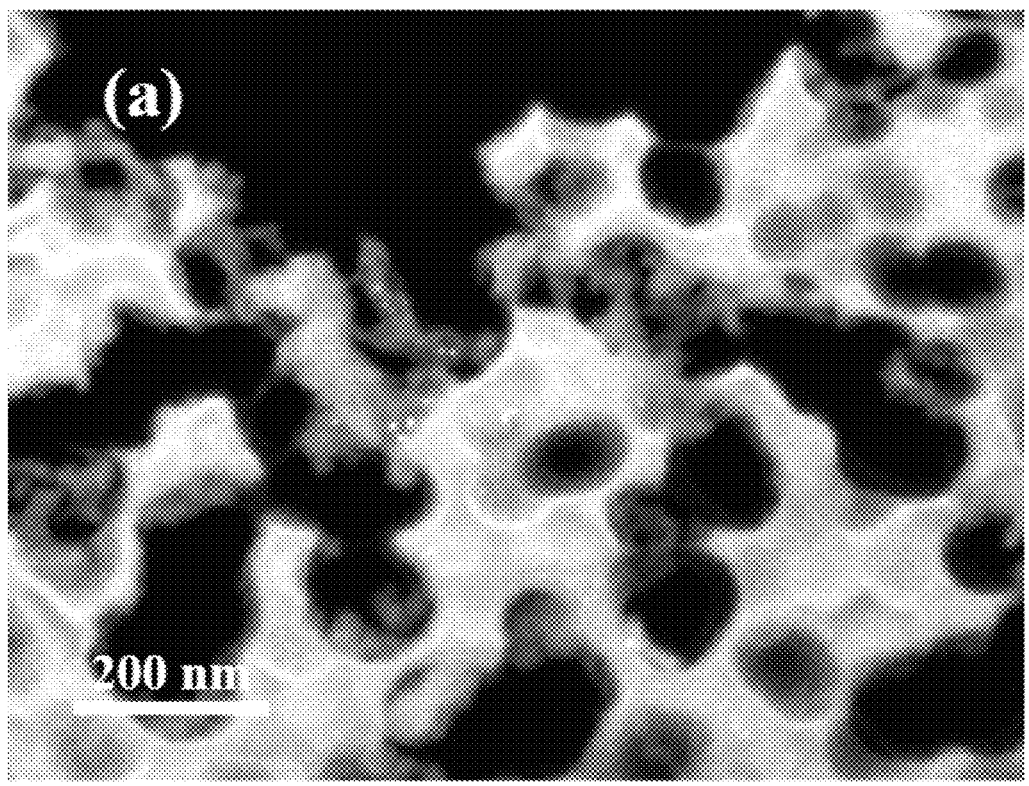
FIG. 12a-12b illustrate the TEM images of a porous poly silicon layer in an active region in an Ion-Selective Field-Effect Transistor (ISFET), according to one embodiment herein.
Figure 12B:
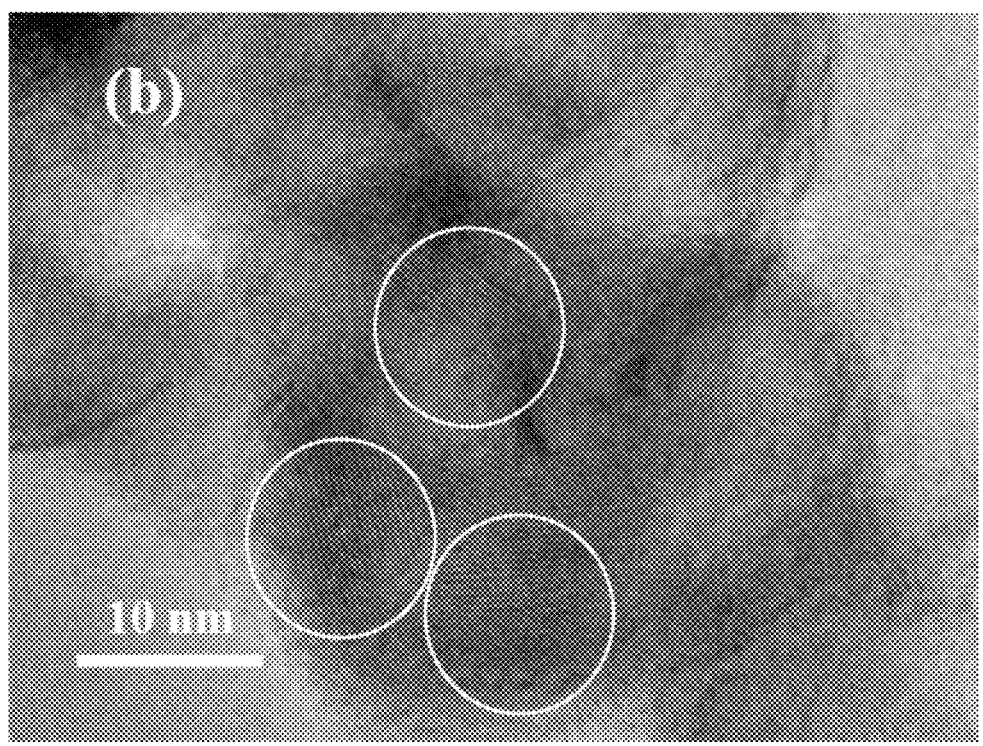
Figure 12C:
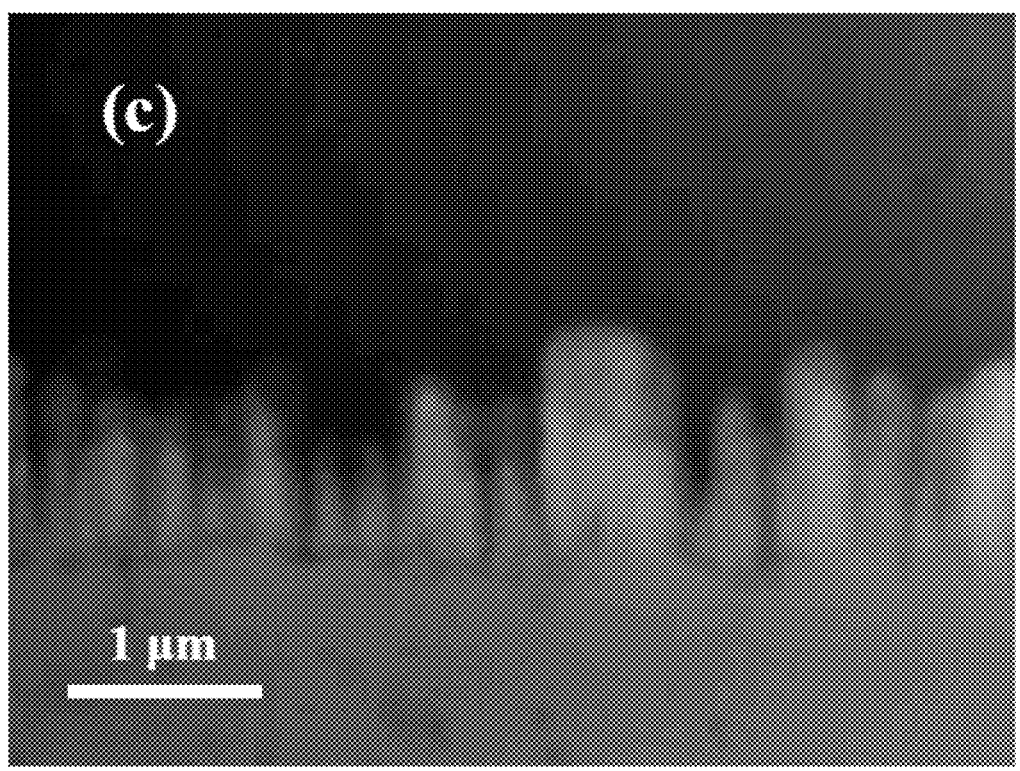
Figure 12D:
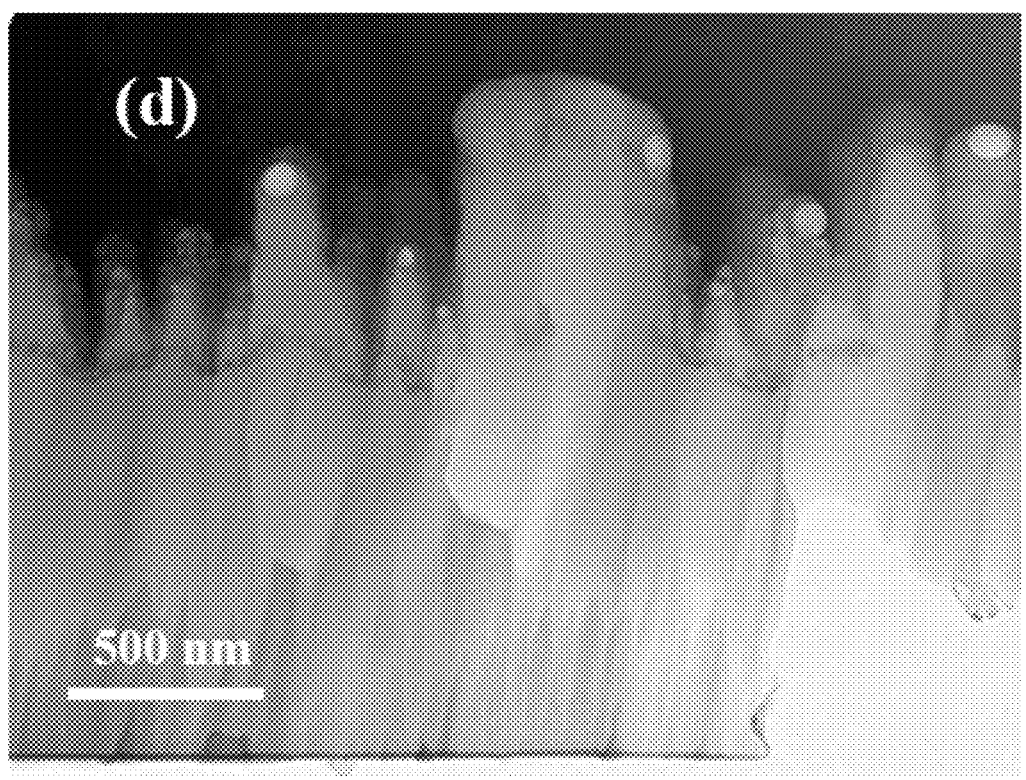

FIG. 12a-12d illustrates the TEM images of porous poly silicon, according to one embodiment herein. With respect to FIG. 12a-12b, the nano porous layer is formed on the gate region and the nano porous layer is made up of porous poly silicon. The plane view of porous poly silicon is shown in FIG. 12a. The image of porous structure formed on the gate region is shown in FIG. 12b. The cross sectional view of the porous poly silicon formed is shown in FIG. 12c-12d.

The various advantages of the present disclosure are to provide a method for fabricating ion-selective field-effect transistor (ISFET) with a nano porous layer. The nano porous layer formed on the gate region of the p-type substrate transmits an ion effect to the underlying silicon dioxide layer. Further the nano porous layer acts as an acceptor of biological objects when the physical adsorption is required. The nano porous layer enhances the stabilization of one or more acceptors when the chemical adsorption is required and also provides a larger effective area on an exposed surface of the p-type silicon substrate. The nano porous layer formed on the gate region provides a high sensitivity to the Ion-Selective Field-Effect Transistor (ISFET) and the fabrication of ISFET increases the slope variation in the electrical characteristics ($I_{DS}$-$V_{GS}$).

The ISFET with porous structures on the gate region is used in the sensors for PH meter, DNA sensors, The foregoing description of the specific embodiments herein will so fully reveal the general nature of the embodiments herein that others can, by applying current knowledge, readily modify and/or adapt for various applications such specific embodiments herein without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the 5 embodiments herein with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A method for fabricating an Ion-Selective Field-Effect Transistor (ISFET) with nano porous structures, the method comprises:
   providing a p-type silicon substrate;
   forming a silicon dioxide layer on the p-type silicon substrate;
   depositing a poly silicon layer on the silicon dioxide layer formed on the p-type silicon substrate;
   patterning the poly silicon layer deposited on the silicon dioxide layer as a gate region;
   forming a source region and a drain region in the silicon dioxide layer;
   depositing a passivation layer on the gate region, the source region and the drain region formed in the p-type silicon substrate;
   etching the passivation layer deposited on the patterned poly silicon layer using a buffered HF; and
   transforming the poly silicon layer into a nano porous layer on the gate region of the p-type silicon substrate by a sequential reactive ion etching process.

2. The method of claim 1, wherein the source region and the drain region are defined by performing a diffusion of the silicon dioxide layer at a temperature of 800° C.

3. The method of claim 1, wherein the passivation layer deposited on the patterned poly silicon layer is also etched using a reactive ion etching process.

4. The method of claim 1, wherein the transforming the poly silicon layer into a nanoporous layer comprises passivating the poly silicon layer with a mixture of $H_2/O_2$ gases with a trace amount of $SF_6$ and etching the poly silicon layer using $SF_6$ as an inlet gas.

5. The method of claim 1, wherein the silicon dioxide layer is formed on the p-type silicon substrate with a thickness of 120 nm.

6. The method of claim 1, wherein the poly silicon layer is deposited on the silicon dioxide layer with a thickness of 1.5 μm.

7. The method of claim 1, wherein the poly silicon layer is deposited on the silicon dioxide layer using a low-pressure chemical-vapour-deposition process.

8. The method of claim 1, wherein the passivation layer is deposited on the patterned poly silicon layer with a thickness of 1.3 μm and wherein the passivation layer is a silicon-oxynitride layer formed on the surface of the poly silicon layer.

9. The method of claim 1, wherein the passivation layer deposited on the patterned poly silicon layer is etched based on gate poly silicon dimensions.

10. The method of claim 1, wherein the nano porous layer formed on the gate region of the p-type silicon substrate transmits an ion effect to the underlying silicon dioxide layer.

11. The method of claim 1, wherein the etching of the passivation layer deposited on the patterned poly silicon layer comprises applying a mask of photo resist on the source region and the drain region in the p-type silicon substrate.

12. The method of claim 1, wherein the sequential reactive ion etching process comprises a hydrogen-assisted dry etching process.

13. The method of claim 1, wherein the nano porous layer formed on the gate region is made of nano porous silicon.

* * * * *